United States Patent
Grim et al.

[19]

[11] Patent Number: 6,139,513
[45] Date of Patent: Oct. 31, 2000

[54] ORTHOPAEDIC SUPPORT WITH HARDENABLE DOUBLE KNIT TYPE MATERIAL

[75] Inventors: Tracy E. Grim, Tulsa, Okla.; Joseph M. Iglesias, Thousand Oaks, Calif.; Kelly M. Speakes, Woodland Hills, Calif.; Michael Campos, Granada Hills, Calif.; Steven T. Relote, Valley Village, Calif.

[73] Assignee: Royce Medical Company, Camarillo, Calif.

[21] Appl. No.: 09/088,905

[22] Filed: Jun. 2, 1998

[51] Int. Cl.[7] ........................................................ A61F 5/00
[52] U.S. Cl. ...................................... 602/6; 602/8; 602/41
[58] Field of Search ........................................ 602/6, 8, 41

[56] References Cited

U.S. PATENT DOCUMENTS

| | | |
|---|---|---|
| 4,235,228 | 11/1980 | Gaylord, Jr. et al. . |
| 4,502,479 | 3/1985 | Garwood et al. . |
| 4,683,877 | 8/1987 | Ersfeld et al. . |
| 4,745,912 | 5/1988 | McMurray . |
| 4,984,566 | 1/1991 | Sekine et al. . |
| 4,996,979 | 3/1991 | Grim et al. . |
| 5,166,480 | 11/1992 | Bottger et al. . |
| 5,284,031 | 2/1994 | Stoll et al. . |
| 5,334,442 | 8/1994 | Okamoto et al. . |
| 5,637,077 | 6/1997 | Parker . |

FOREIGN PATENT DOCUMENTS

| | | |
|---|---|---|
| 0752839 | 3/1995 | European Pat. Off. . |
| 800572 | 11/1954 | United Kingdom . |

*Primary Examiner*—John G. Weiss
*Assistant Examiner*—Keleen Hart
*Attorney, Agent, or Firm*—Oppenheimer Wolff & Donnelly LLP

[57] ABSTRACT

An orthopaedic support is formed of a double knit type fabric material with spaced interwoven layers formed of high strength materials and an open-work matrix of filaments or threads interconnecting the layers. The fabric is impregnated with a water hardenable material. The support material or product is packaged in a water-vapor impermeable package; and is opened and water is supplied to the fabric when it is applied to the part of the anatomy requiring support. The fabric may be included in a soft goods support including a water distribution network and straps to hold the support in place.

28 Claims, 12 Drawing Sheets

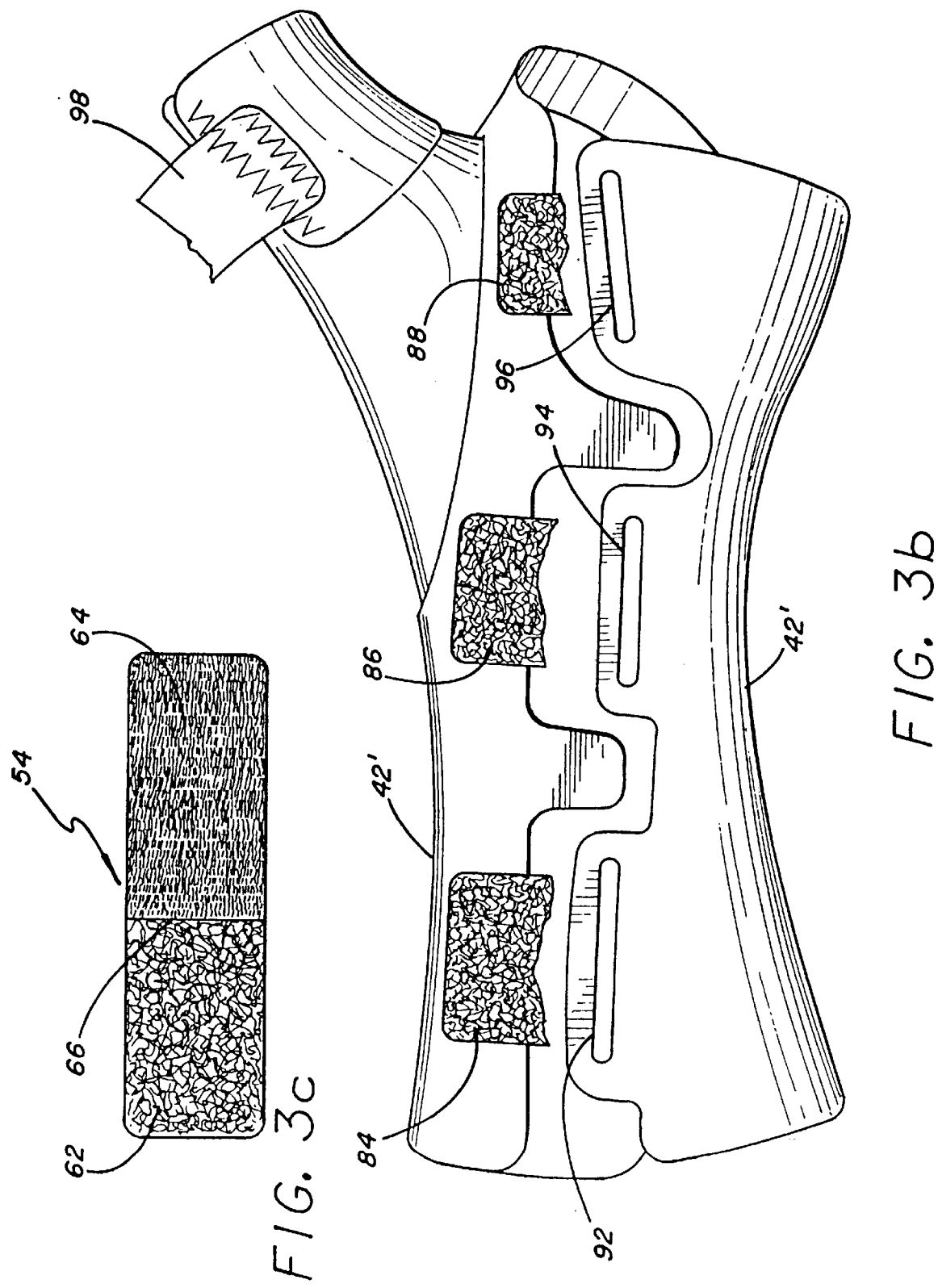

FIG. 6
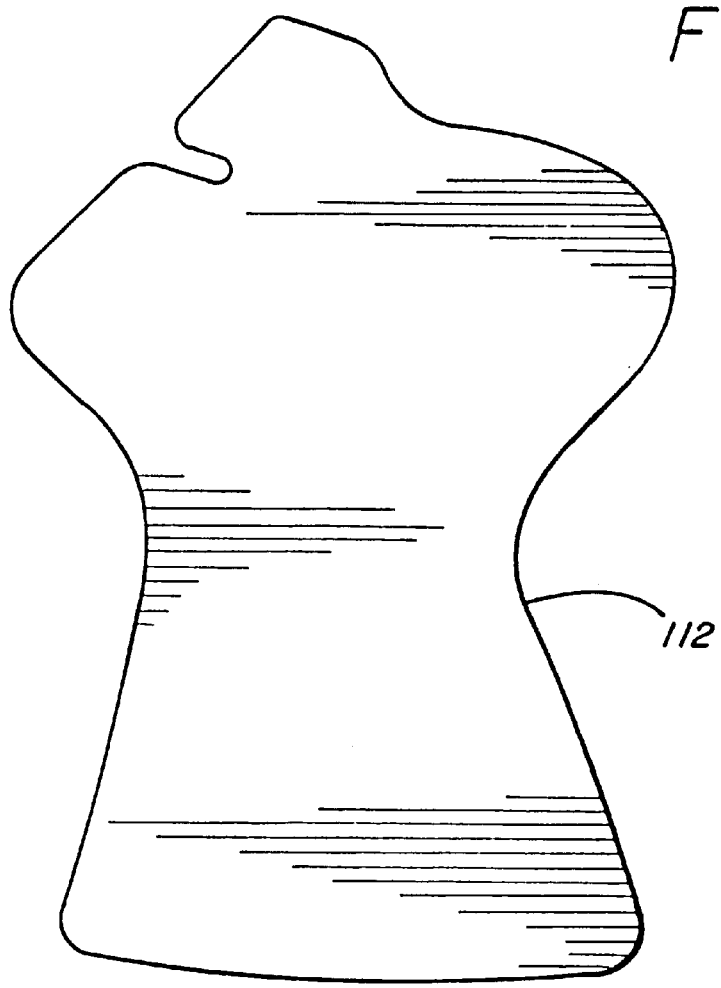
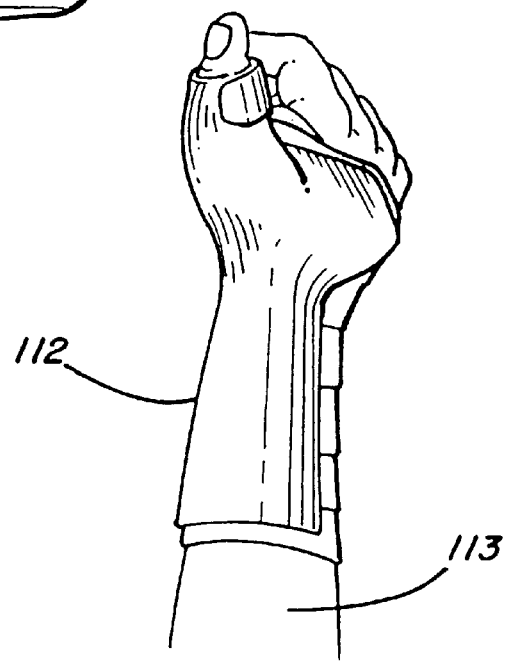
FIG. 7

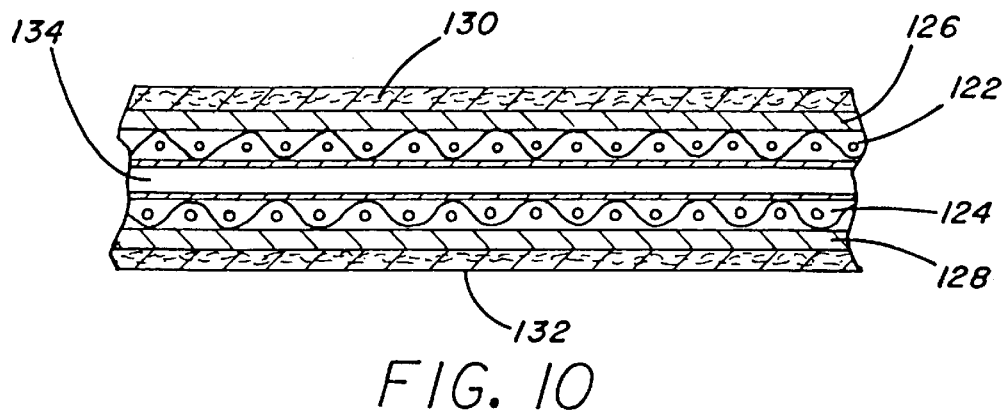
FIG. 10
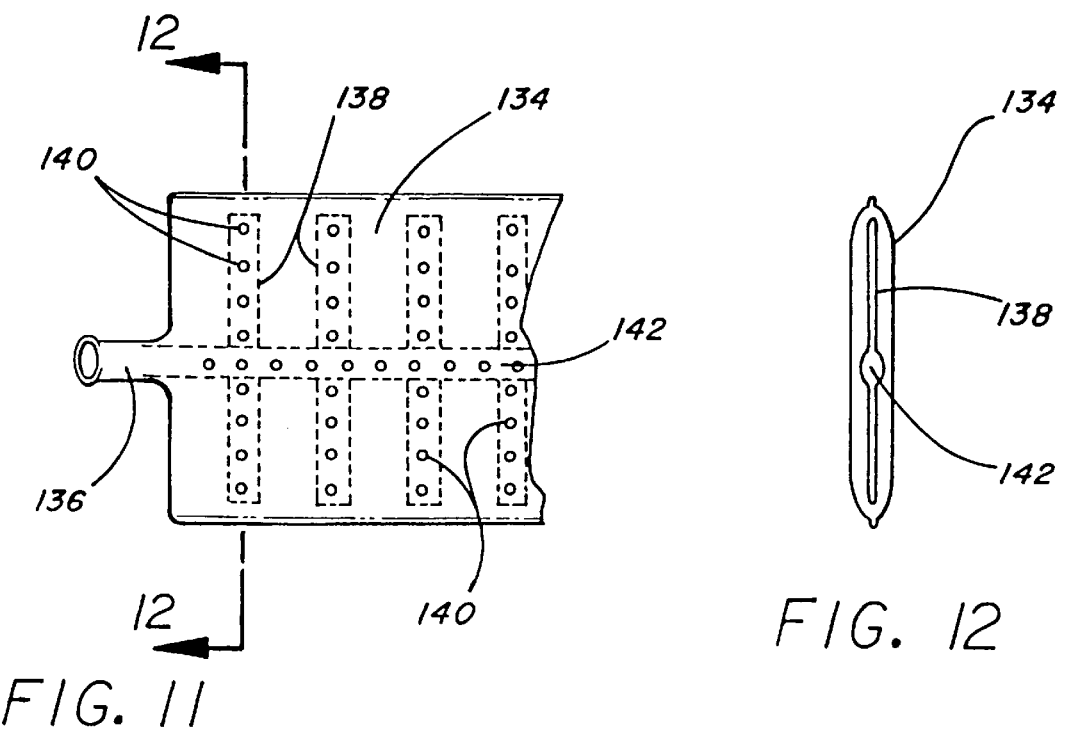
FIG. 11
FIG. 12

ORTHOPAEDIC SUPPORT WITH
HARDENABLE DOUBLE KNIT TYPE
MATERIAL

FIELD OF THE INVENTION

This invention relates to the use of double knit type fabrics for forming orthopaedic splints or supports.

BACKGROUND OF THE INVENTION

It has previously been proposed to use water-hardenable materials in orthopaedic supports and casts; and typical patents disclosing such products include U.S. Pat. No. 4,996,979, granted Mar. 5, 1991, and U.S. Pat. No. 4,683, 877, granted Aug. 4, 1987. However, when materials as disclosed in these patents are employed, the flow of liquid through the open cell foam or layers of fabric, as well as the strength of the orthopaedic support may not be subject to the desired level of control.

It is also noted that these prior art products mentioned above have other problems. Thus, for example with regard to the casts or supports using layers of material, care must be taken to firmly engage the layers during the setting period to ensure unitary bonding of the entire layered cast or assembly. Doctors practicing in this area even have a saying: "rub it like you love it," to encourage full engagement of the layers during hardening of the water-hardenable material. This step obviously requires care and expertise, as it is undesirable to apply undue force to an injured limb involving a broken limb, for example. Further, if this technique is not properly employed, the layers will not fully bond together, and the cast or support will be weak, and the layers could separate. Also with regard to the hardenable splints or supports using open cell foam, they may lack sufficient flexibility and conformability to properly fit the three-dimensional parts of the anatomy requiring splinting or support.

Flat rigid panels have also been proposed using double knit fabrics and hardenable resins, as indicated by U.S. Pat. No. 5,166,480, granted Nov. 24, 1992, and entitled "Orthopaedic Sheet-Like Composition." Attention is also directed to U.S. Pat. No. 5,334,442, granted Aug. 2, 1994. This patent discloses an intermediate pliant sheet which may be made of a fabric such as glass fiber impregnated with a water-hardenable material. Then, on both sides of this pliant layer, the patentees disclose the use of layers of double knit material. Thus, with double knit material present in the assembly, it is not used to receive the water-hardenable material but is only used for padding.

As noted above, prior art orthopaedic products have involved shortcomings in the flow control of water to the water-hardenable material and the strength of the orthopaedic device.

SUMMARY OF THE INVENTION

Accordingly, a principal object of the present invention is to improve both the control of the flow of water to the curable resin in orthopaedic supports or splints, and concurrently to provide the desired strength for the product.

Additional objects include increasing the reliability and simplifying the application, increasing conformity, reducing the thickness and weight while increasing the strength of casting materials.

In accordance with a method for forming an orthopaedic support illustrating the principles of the invention, an integral double layer fabric with a central open-work matrix, such as a double knit material, is impregnated with a water-hardenable material under low humidity conditions, and is packaged in a water-vapor impermeable package. The impregnated double knit type material is located adjacent the injured portion of the anatomy, such as a broken bone, so that the material conforms to the desired configuration of the injured part of the anatomy. Water is applied through the open-work matrix of the double knit material to rapidly wet the water-hardenable material, to cause stiffening of the orthopaedic support and preventing undesired movement of the injured part. Water is applied to the double knit type material prior to application to the anatomy in the case of tapes and flat splinting shapes; and in the case of soft goods type products, following application of the soft goods support to the anatomy.

The orthopaedic support preferably includes high strength material such as glass fiber fabric, kevlar fibers, aramids, or other high strength fibers, to provide strength to complement the rigidity or stiffness of the water-hardenable material.

The orthopaedic support using the double knit type fabric with its open-work central matrix may take a number of forms, including a tape, a flat or contoured splint shape configured to fit an injured portion of the anatomy, or a soft goods product having straps to secure the support in place, and having the double knit fabric within its construction.

Regarding the soft goods type support, it may be similar to that showing in U.S. Pat. No. 4,996,979, and may include either a single layer of impregnated double knit type fabric, or a plurality of such layers, with one or more intermediate water distribution networks. In addition, the soft goods support may include one or more of the following additional features: (1) an outer semi-flexible or semi-rigid member of plastic or the like to provide a general shape to the assembly prior to hardening of the material; (2) water impermeable layers for confining the water; (3) soft cloth lining material for engaging the skin of the injured party; and (4) straps for holding the assembly onto the injured part of the anatomy.

Incidentally, regarding water-hardenable materials and other matters, the disclosure of U.S. Pat. No. 4,996,979 is hereby incorporated into this specification by reference.

Concerning water-vapor impermeable material for packaging the products, metallized mylar or aluminum foil may be employed, in addition to other known barrier materials.

Regarding the flat or contoured blanks to be used as a splint or a support, they may have cut-outs and darts to more closely fit the portion of the anatomy, such as the forearm, wrist or elbow, to which it is to be mounted.

Concerning advantages of the invention, it is noted that a single layer of the double knit material has superior properties to the conventional layers of fiberglass fabric; and it is more stretchable than the fiberglass/foam laminate constructions for orthopaedic casting products which have been proposed heretofore. It also is lighter, thinner and stronger than conventional casting materials.

As an additional advantage of the invention, the application of splints or supports using double knit type material does not require the special expertise and careful rubbing technique needed to produce a strong layered splint or support. Further, the fact that the inner layer and the outer layer of the double knit type support material are relatively easily moveable with respect to one another, as they are only coupled by the spacer yarns, means that the material more easily conforms closely to the three-dimensional configuration of the anatomy without wrinkling or undue distortion.

It is further noted that hardenable casts and splints formed of appropriate double knit type material have higher strength than the prior art foam or multi-layer hardenable splints.

Other objects, features and advantages of the invention will become apparent from a consideration of the following detailed description, and from the accompanying drawings.

BRIEF DESCRIPTION OF THE DRAWINGS

FIG. 3B is a view of an alternative fiberglass soft goods device illustrating the principles of the invention;

FIG. 3C shows a strap using hook and loop type material, which may be employed in the orthopaedic soft goods products of FIGS. 3A and 3B;

FIG. 6 shows a flat blank formed of the double knit material of the type shown in FIGS. 1 and 2;

FIG. 7 shows the blank of FIG. 6 mounted on the forearm of a patient to provide supplemental support or splinting of this portion of the anatomy;

FIG. 10 is a cross-sectional view of a multi-layer construction involving two layers of double knit material, a central water distribution network, outer water impermeable layers, and cloth fabric on the outside of the assembly;

FIG. 11 is a schematic view of a water distribution network included as a central portion of the assembly of FIG. 10;

FIG. 12 is a cross-sectional view taken along lines 12—12 of FIG. 11;

DESCRIPTION OF PREFERRED EMBODIMENTS OF THE INVENTION

Figure 1:
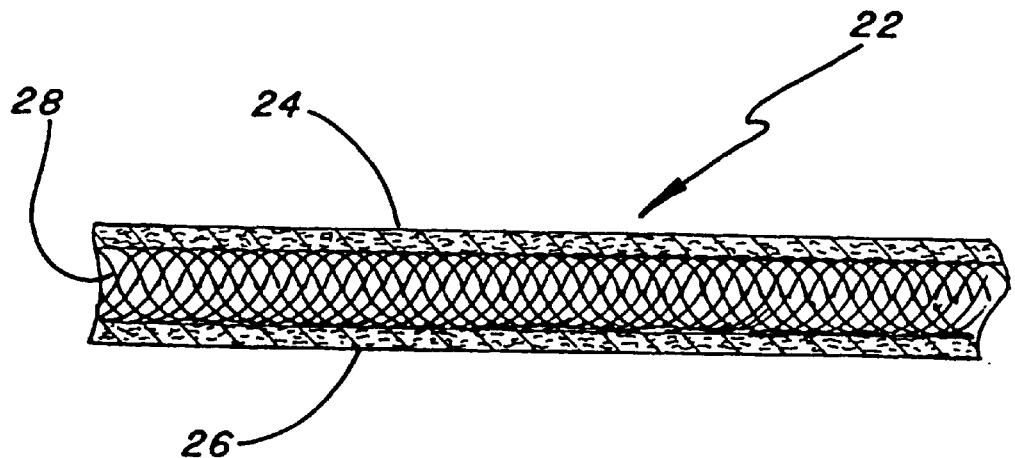
FIG. 1 is a cross-sectional view of a double knit type material which is to be employed in the fabrication of orthopaedic splints or supports in accordance with the present invention.

Referring more particularly to the drawings, FIG. 1 shows a double knit fabric 22 including the surface knits 24 and 26 and spacer yarns 28. The surface knits 24 and 26 can be of the same or different knit patterns. These patterns can range anywhere from smooth, essentially continuous surfaces to meshes and other more complex knits. They may be knit from materials such as polyester, nylon, and various aramid fibers, including fiberglass. The spacer yarns 28 keep the surface knits a specific distance apart, and allow for individual surface movement. They are usually composed of monofilament yarns, but can also be of multi-filament yarns. The spacer yarns 28 typically are made from polyester, nylon, or other thermoplastic materials that can be drawn into a yarn of the desired diameter. In addition, they may be made from glass and other aramid fibers.

Figure 2:
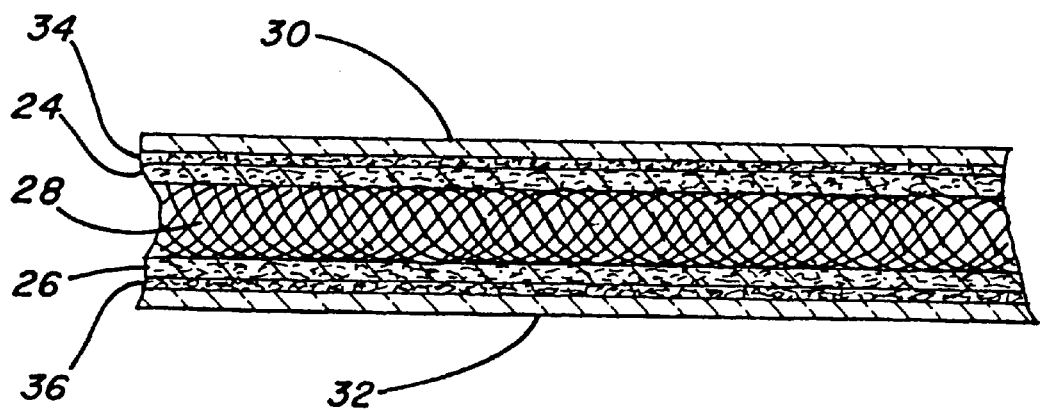
FIG. 2 is a cross-sectional view of a central layer of double knit material reinforced by layers of high strength material such as fiberglass fabric on both sides of the double knit material.

FIG. 2 shows how double knit materials may be reinforced with glass knits or other high strength fabrics to increase their strength. More specifically, fiberglass cloth material 30 and 32 may be bonded to the double knit material by adhesive webs 34 and 36. This bonding could also be achieved by any other known technique such as by flame bonding, or by sewing, for specific examples. The lamination of the glass knit fabrics 30 and 32 to the double knit material by the adhesive layers 34 and 36 also reduces the fraying of the glass knit when the assembly is cut, and holds the entire assembly intact during subsequent operations.

In accordance with the present invention, the double knit type material is impregnated with a water hardenable material, such as unpolymerized urethane material. These water hardenable materials are well known, and have been used heretofore in orthopaedic devices. Reference is again made to U.S. Pat. No. 4,996,979, granted Mar. 5, 1991, for detailed information regarding one type of water hardenable material which may be employed.

One aspect of the present invention, as mentioned above, is the recognition that double knit material, with its central openwork matrix formed by the spacer yarns, is ideally suited to initially receive the hardenable urethane chemistry, and subsequently to receive the water activation which serves to initiate the hardening and polymerization of the urethane material. Thus, in the various embodiments to be described hereinbelow, the double knit type material is initially impregnated with a water hardenable compound, and the orthopaedic device or material is mounted adjacent the portion of the anatomy to be supported, and is hardened in place to conform to the configuration of the anatomy.

Figure 3A:
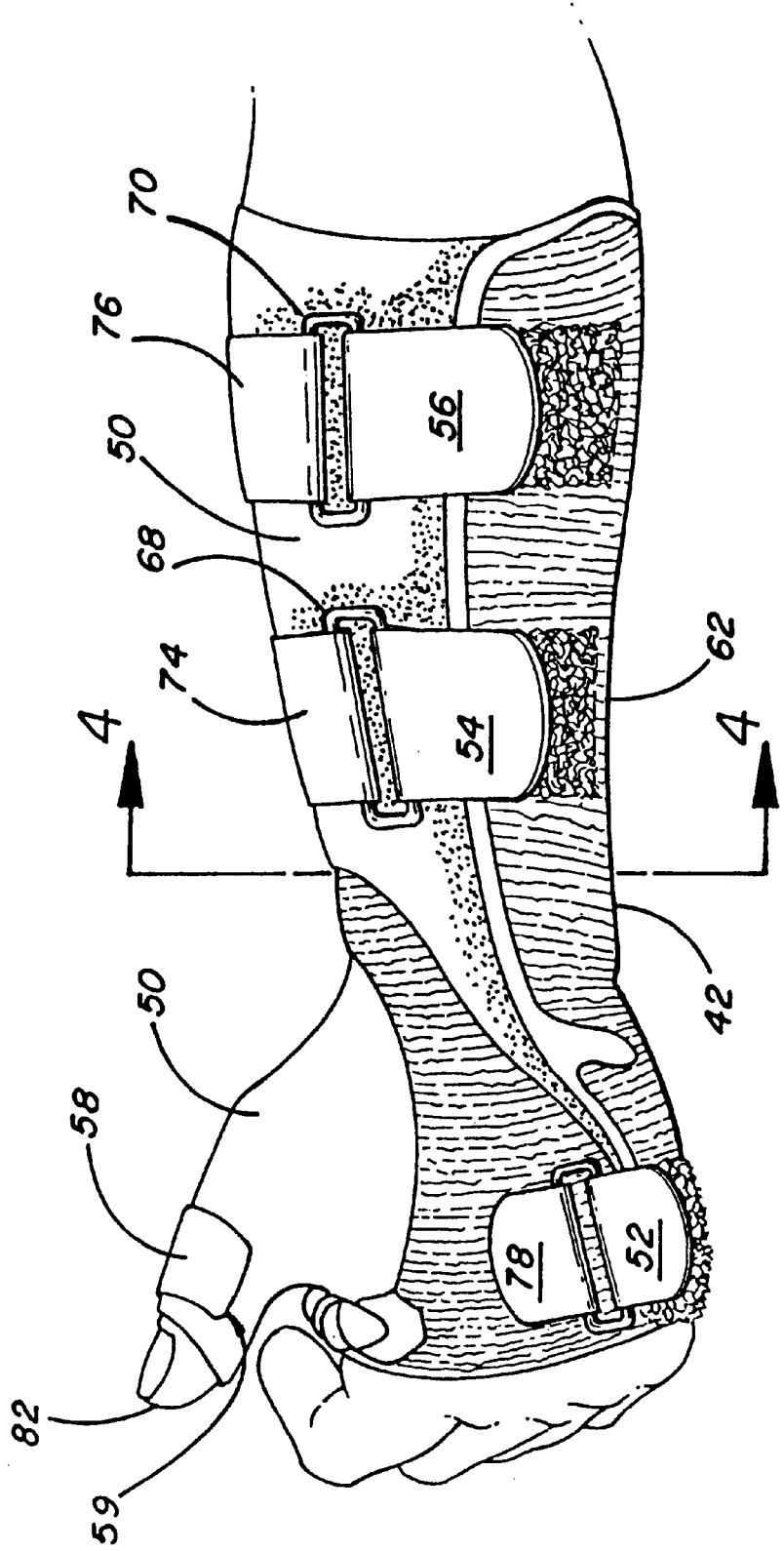
FIG. 3A is a side view of a fiberglass soft goods assembly for the forearm and wrist, employing a double knit fabric of the type shown in FIGS. 1 and 2.
Figure 4:
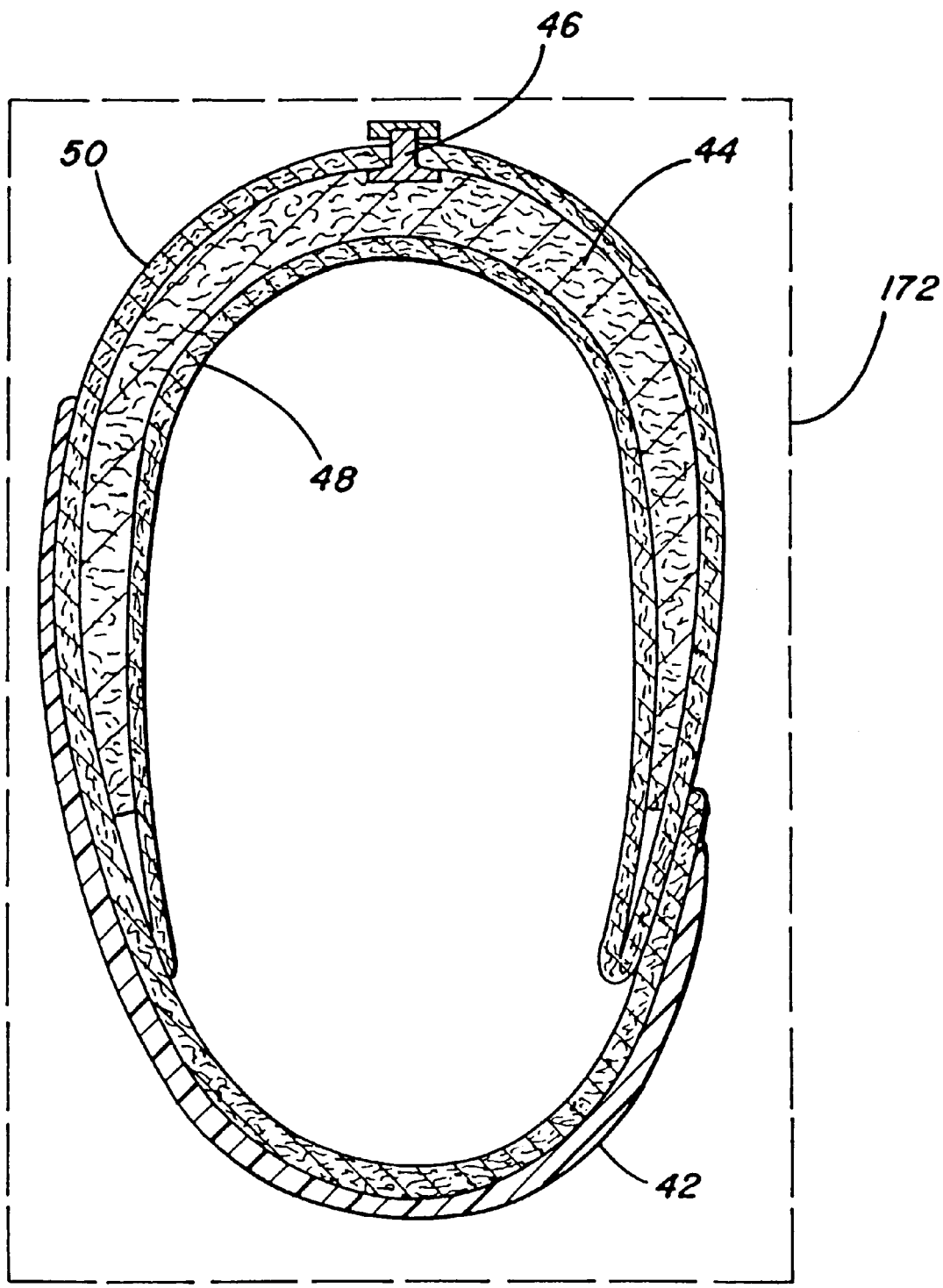
FIG. 4 is a cross-sectional view taken along lines 4—4 of FIG. 3A.

Reference will now be made to FIGS. 3A, 3B, and 3C, and FIG. 4 which is a cross-section taken along lines 4—4 of FIG. 3A. In FIGS. 3A, 3B, and FIG. 4, there is shown a shell-shaped or channel-shaped lower plastic member 42 which may be made of any semi-flexible or semi-rigid plastic material, such as polypropylene, about ¹⁄₁₆-inch in thickness. Mounted on the plastic channel member 42 is a layer of the double knit material assembly 44, 48, 50 which is impregnated with a water hardenable urethane material. An inlet construction 46 is provided for receiving a standard or measured amount of water, in order to penetrate and activate the hardening of the urethane material in the double knit material 44. This can be provided by the use of a syringe having a needle which is inserted through the entry port 46. The inner layer 48 and the outer layer 50 of the assembly include both a water impermeable layer immediately adjacent the double knit material, and also a layer of cloth for comfortable engagement with the skin of the user and for providing a convenient surface for manipulating the orthopaedic support on its outer surface.

In addition to the materials mentioned in connection with FIG. 4 of the drawings, FIG. 3A shows four straps 52, 54, 56 and 58 which are employed to secure the orthopaedic device onto the forearm of the patient. These strap arrangements may extend from one edge of the channel member 42, to its other edge. The three straps 52, 54, and 56 have a configuration as indicated in FIG. 3C of the drawings. More specifically, strap 54, as shown in FIG. 3C of the drawings, includes a strip of loop type material 62 which is stitched together with a strip of hook type material 64. This type of hook and loop securing material is well known and is commonly sold under the trademark "VELCRO." The two straps may be held together in any desired manner by bonding or by the stitches 66, for specific example, as shown in FIG. 3C. In practice, referring back to FIG. 3A, one portion 62 having loop type material on its outer surface may be secured to the member 42 by adhesive or the like, and the free end 64 of the strap 54 extends up through the rectangular loop 68, and then back over the plastic member 42 to engage the hook type material on the lower surface of the strap 54 with the loop type material 62 of the strap. Incidentally, the rectangular loops 68, 70 and 72 are mounted on loops of the strap members 74, 76 and 78 which may be secured to the other edge (not shown) of member 42. Incidentally, the strap 58 has a simpler configuration and merely holds two portions of the layered material 50 together to provide proper support for the thumb 82 of the patient. The strap 58 and a matching area 59 on material 50 may be provided with mating hook and loop type material to adjustably maintain the strap in the desired closed position to restrain the thumb against excessive movement.

The embodiment of FIG. 3B is similar to that of FIG. 3A, and includes the plastic channel member 42' providing initial support, and the multi-layer material including the double knit central core, as indicated by the reference numeral 50 showing the outer surface of this multi-layer assembly. In the arrangements of FIG. 3B, the straps 84, 86 and 88 are shown broken away, but in use would extend through the integral loops 92, 94 and 96, respectively. The straps 84, 86 and 88 may be of the same type shown in FIG. 3C with exposed loop type material being secured to the plastic channel member 42', and the portion of the strap extending through the integral loops having mating hook type material on its surface. The strap 98, which is also shown broken away, serves to hold the thumb portion of the brace in its proper position to support the injured thumb and/or forearm of the user.

It is further noted in passing that the double knit type material as described herein may be substituted for the material shown at reference numeral 24 in FIG. 4 of U.S. Pat. No. 4,996,979, as cited hereinabove.

Figure 5:
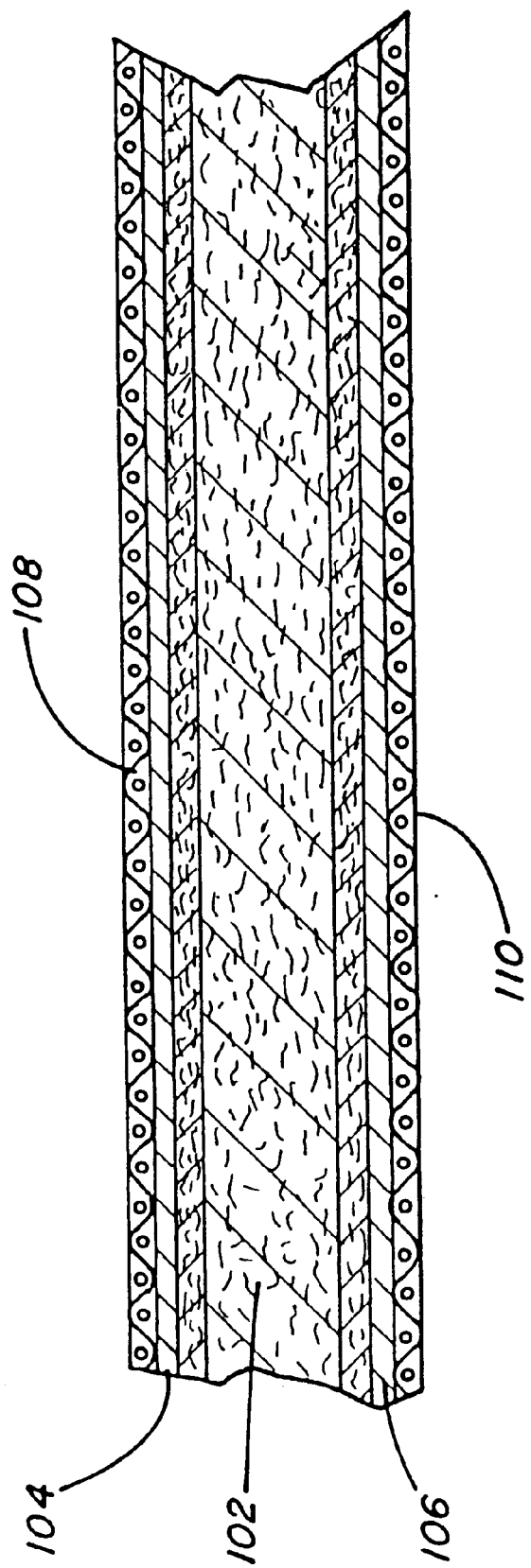
FIG. 5 is a cross-sectional view of an assembly including double knit material in the center, layers of water impermeable plastic, and finally an outer layer of cloth, which may be employed in the implementation of the present invention.

In the showing of FIG. 5, a central body of double knit material 102, with two outer surface knits, and a central matrix of spacer yarns is provided with an upper water impermeable plastic layer 104 and a lower water impermeable plastic layer 106 to retain water which is provided to the double knit material 102 and prevent it from contacting the user, as well as confining the water action to the hardening of the impregnated material. In addition, outer cloth or fabric layers 108 on one side and 110 on the other side are provided for ease in handling the layered material and for comfort in engaging the skin of the user or patient.

FIGS. 6 and 7 show, respectively, a blank 112 for providing splinting or casting action for the forearm 113 of a patient, and the blank 112 being mounted on the forearm 113. The blank 112 as shown in FIG. 6 is specifically configured to be mounted on the forearm, and may be held in place by appropriate elastic tape, or tape provided with hook and loop surfaces, for specific examples, once it is applied to the forearm of the patient. Of course, the blank is formed of the impregnated double knit material of one of the types described in the present specification, and is initially packaged in a water impermeable package.

Figure 8:
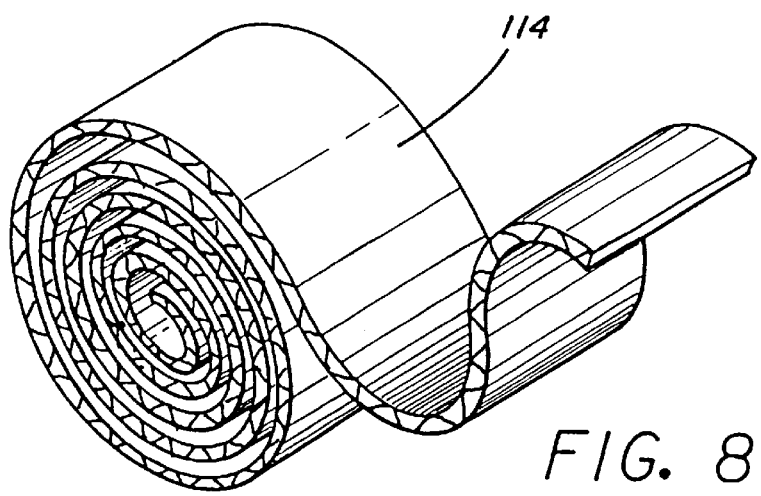
FIG. 8 is a perspective view of an orthopaedic casting tape formed of double knit material.
Figure 9:
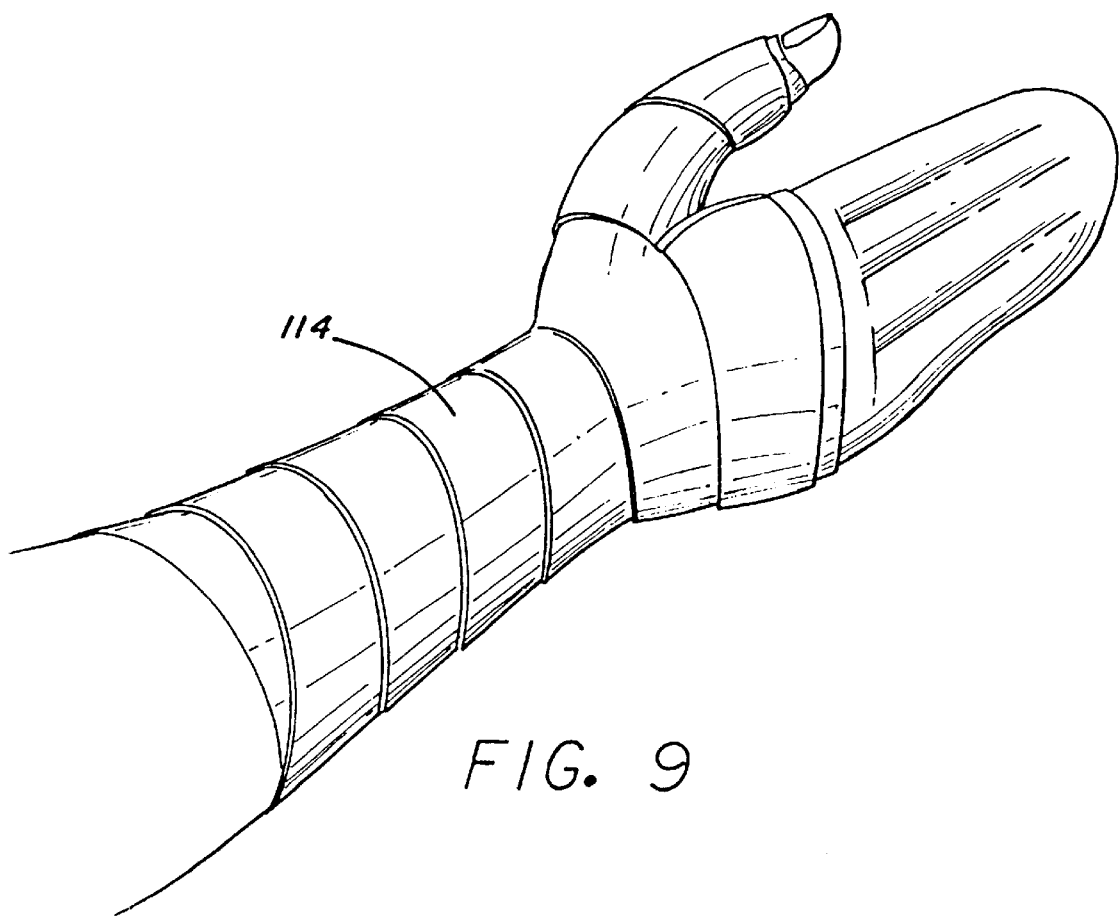
FIG. 9 shows the tape of FIG. 8 mounted on the forearm of a patient to provide casting or supplemental support.

FIG. 8 shows a tape 114 formed of impregnated double knit material; and FIG. 9 shows the tape of FIG. 8 applied to the forearm of a patient for splinting or support purposes.

FIGS. 10 through 12 show an alternative type of layering which may be employed, for example, in the fiberglass soft goods device of FIGS. 3 and 4. More specifically, the arrangement of FIG. 10 includes two layers of double knit material designated 122 and 124, an outer water impermeable layer 126 on one side of the assembly, and a water impermeable layer 128 on the other side, with outer fabric layers 130 and 132. A water distribution channel or network 134 is provided to direct activation water into the two impregnated double knit fabric layers 122 and 124.

FIGS. 11 and 12 show additional views of this water distribution network 134, with an inlet 136 which may be provided with a suitable one-way flapper type valve of a type known in this field, and distribution channels 138 with openings 140 for directing water throughout the two impregnated double knit fabric layers. FIG. 12 is a cross-sectional view of the thin walled water distribution network, with a central channel 142 and the branch channels 138.

Figures 13, 14:
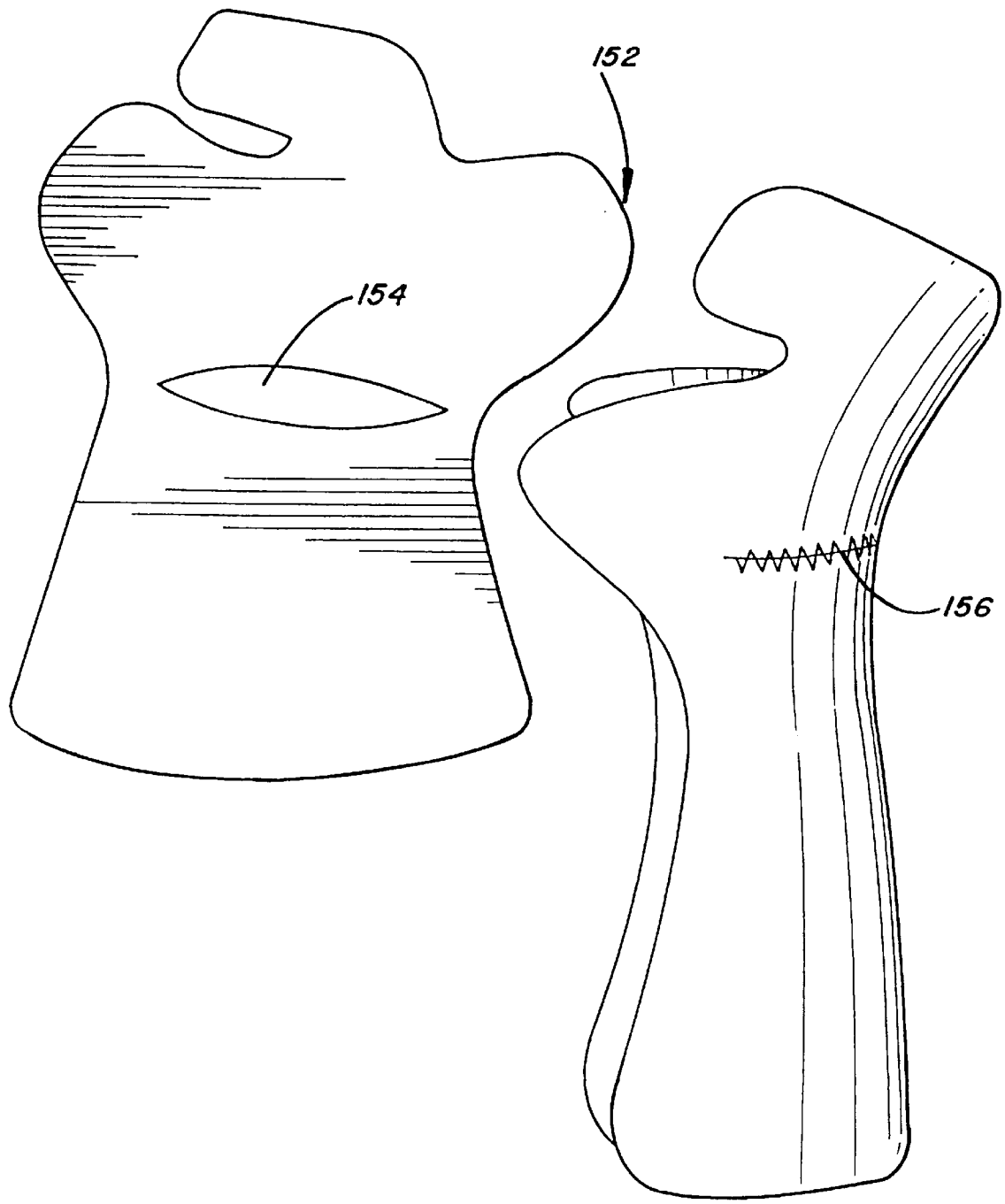
FIG. 13 is a flat blank including a cutout area to help in forming the blank into a cast or support for the thumb.
FIG. 14 shows the blank of FIG. 13 formed into a three-dimensional configuration for application to the forearm and thumb of a patient.

FIG. 13 shows an alternative thumb-spica blank 152 with a die cut opening 154 extending through the thumb-spica blank. The opening 154 may be sewn up, as indicated in FIG. 14 by the stitches 156, or it may be left unstitched if desired. This provision of the opening is of assistance in forming the thumb-spica into its desired and necessary three-dimensional configuration as it is applied to the forearm of the patient, and avoids wrinkling or bunching up of the support blank.

Figure 15:
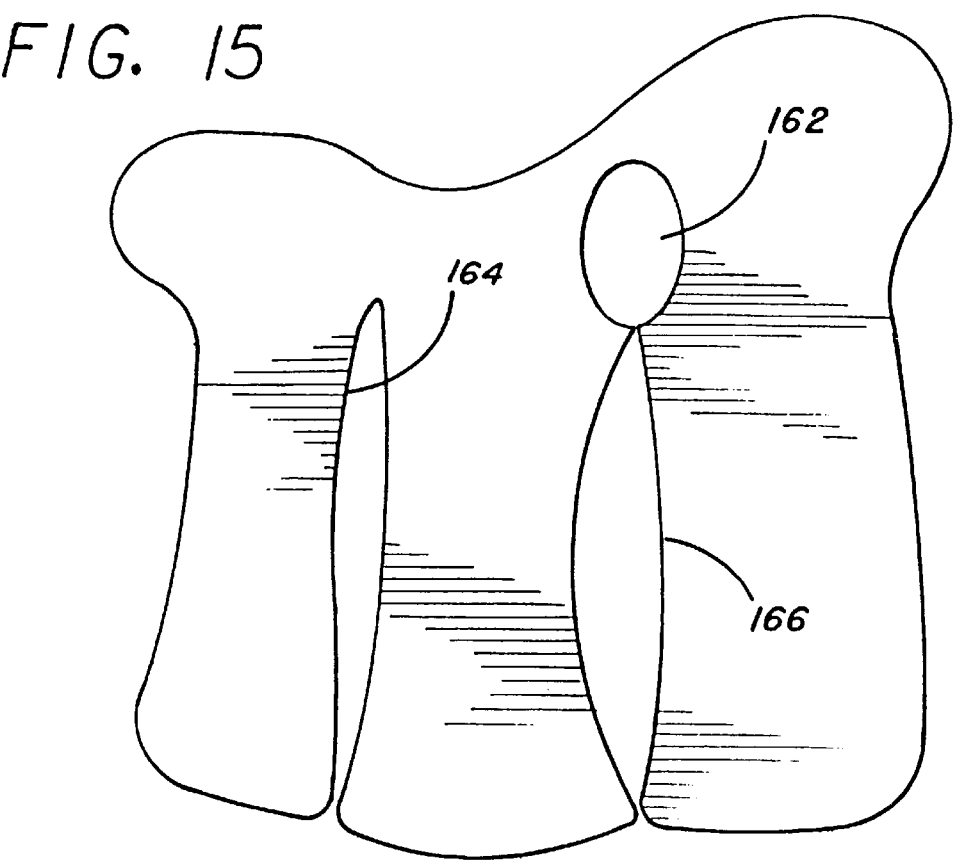
FIGS. 15 and 16 show a flat wrist brace with die cuts, and a corresponding wrist brace in a three-dimensional configuration, respectively.
Figure 16:
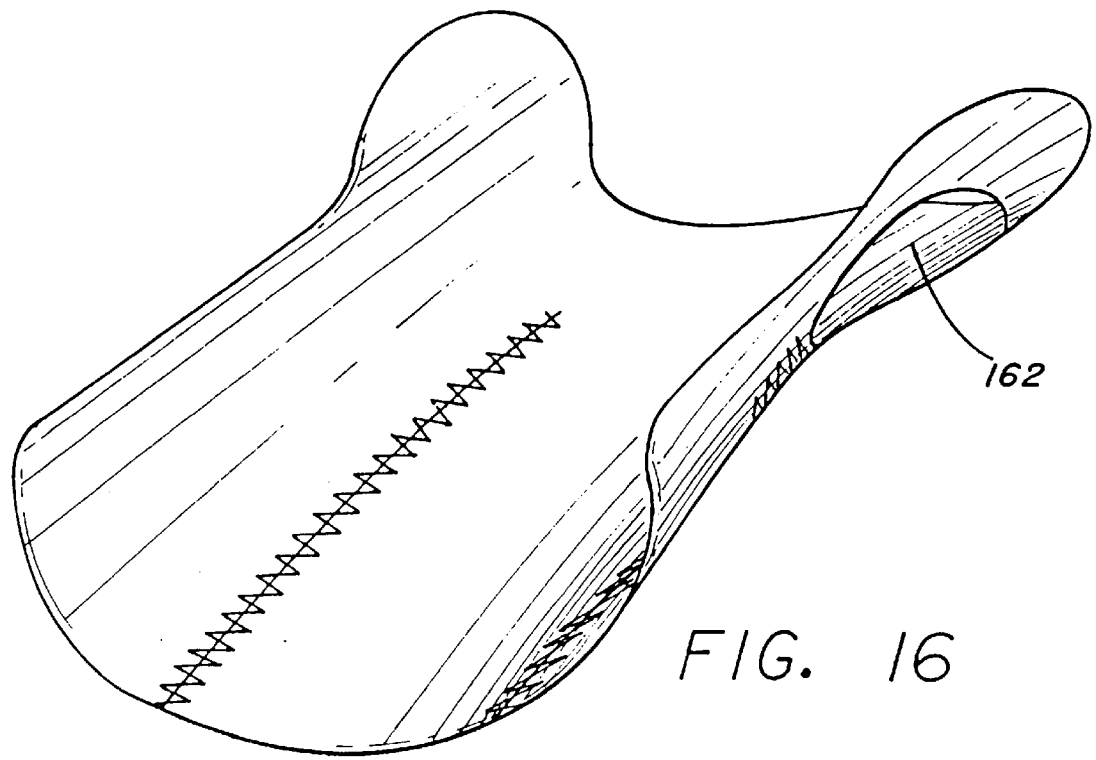

The wrist brace of FIG. 15 is similarly provided with die cut openings or slits 162, 164, and 166. Following stitching or otherwise bonding of the adjacent edges together, the wrist brace is formed into a three-dimensional configuration, as shown in FIG. 16. The opening 162 is to receive the thumb of the patient to assist in locating the wrist brace on the forearm.

Figure 17:
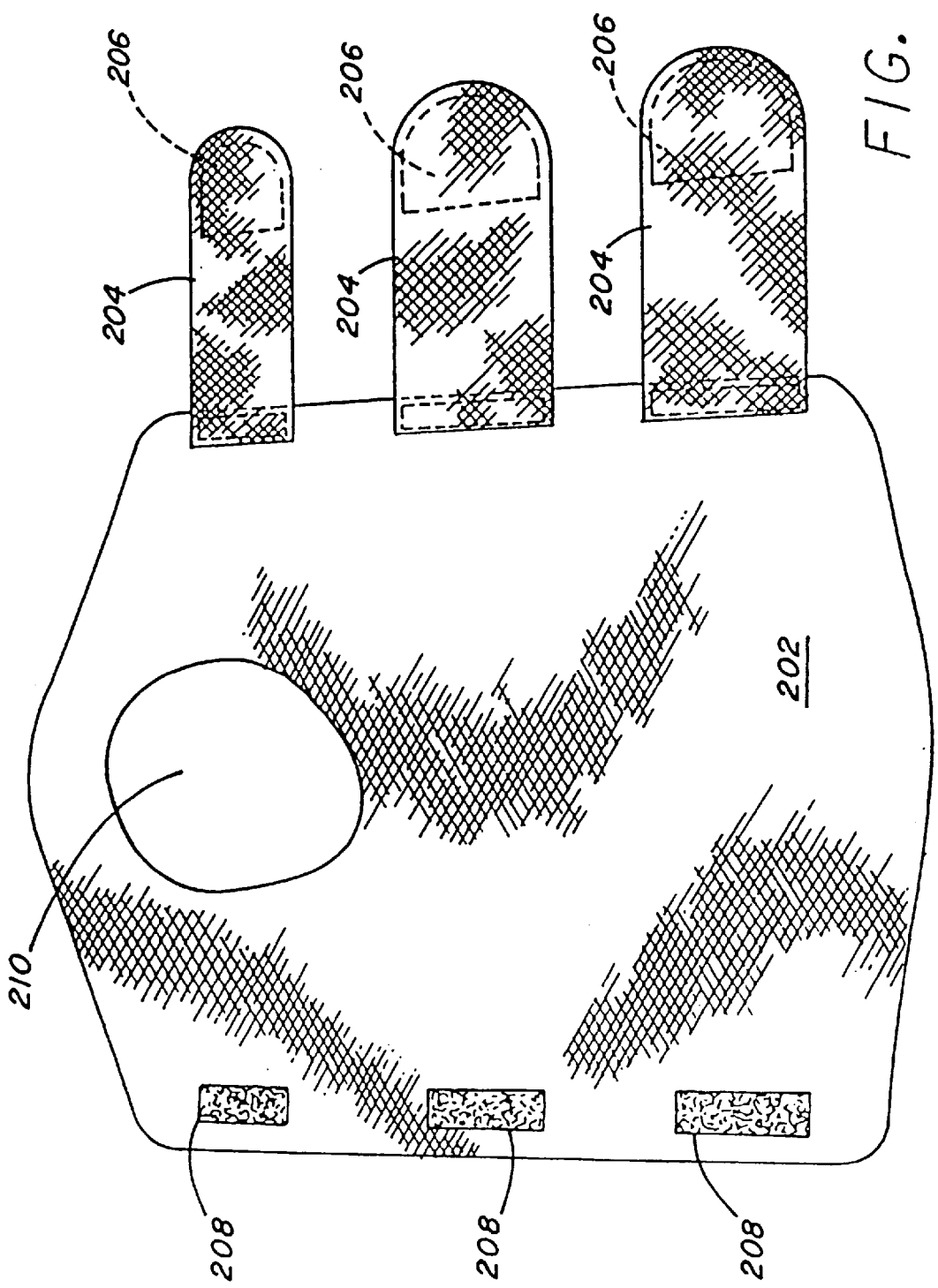
FIG. 17 shows a blank formed of double knit type material provided with straps.
Figure 18:
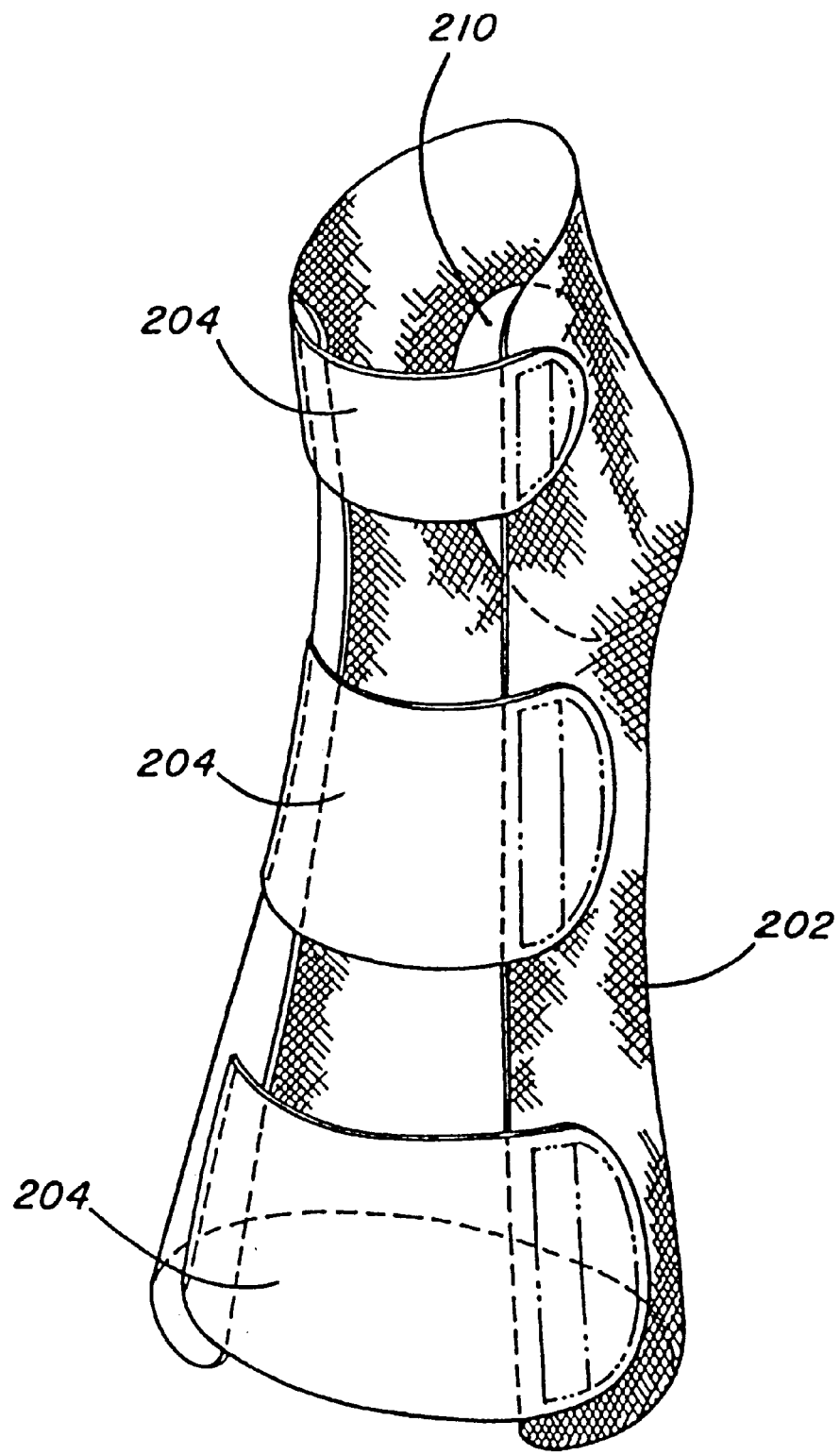
FIG. 18 shows the support or splint of FIG. 17 formed into a three-dimensional configuration.

FIG. 17 shows a flat layer 202 of double knit-type material, with straps 204 for securing the resultant splint or support in a three-dimensional configuration onto the wrist or forearm of the patient. The double knit-type material is impregnated with water-hardenable material, and sold in a water vapor impermeable package. At the time of use, it is immersed in water to initiate the hardening, and mounted on the patient, with the pads 206 on the straps mating with pads 208 on the double knit-type material 202. The pads may be formed of mating hook and loop-type material, known as VELCRO®. The thumb of the patient extends through the opening 210. FIG. 18 shows the splint or support of FIG. 17 in a formed three-dimensional configuration, with the opening 210 extending downward in FIG. 18. Thus, the construction of FIGS. 17 and 18 results in an inexpensive, simple, and effective splint or support. A thin layer of non-impregnated soft cloth material may be provided on the side of the double knit material which is to engage the skin of the patient.

Now, referring back to FIG. 4 of the drawings, the dashed lines 172 represent a water vapor impermeable package for containing the orthopaedic product. This could be formed of metallized mylar, aluminum foil, or any known water vapor impermeable material, which will prevent premature activation and hardening of the urethane material which is impregnated into the double knit material. While the water-impermeable packaging is shown with regard to FIG. 4, it is also applicable to all of the other embodiments of the invention, following application of the water-hardenable material.

For all of the products as described hereinabove, the double knit type material is initially impregnated with the water hardenable urethane material, and then the entire soft good product, tape or blank, is packaged in the water vapor impermeable package. When it is time to apply the product to a patient, the product is mounted onto the part of the anatomy requiring support or splinting, and water is supplied to the impregnated double knit material. With the openwork matrix of the double knit material, rapid and thorough penetration of the water and activation of the urethane occurs. In the case of the soft goods type of products, the straps are employed to mount the units securely on the injured portion of the anatomy, and the water hardenable material conforms to the configuration of the patient. Similarly, in the case of the blanks or the tapes, they are immersed in water and then applied to the injured portion of the anatomy before the hardening occurs.

Concerning the strength of the double knit-type material as compared with several layers of fiberglass fabric, certain flexural modulus tests were done, with six inch by four inch samples. In the tests, the test samples were impregnated with the same water hardenable material, were activated by water, and permitted to harden, with the same procedures being used for all samples. The test samples using the double knit-type material weighed about 34 grams; and the weight of the fiberglass samples, using six layers of fiberglass, was about 40½ grams, or about 22% heavier than the double knit-type material test samples. The strength of the double knit-type samples was about 71 pounds at the yield point for the hardened samples, while the yield point for the layered fiberglass test samples was about 47 pounds. Accordingly, the double knit-type material was nearly 50% stronger than the fiberglass samples, as well as being lighter.

Concerning the details of the test samples, the layered fiberglass samples were formed of six layers of Pinnacle Brand Fiberglass Tape. The double knit-type material had fiberglass top and bottom layers, and the spacer yarn was monofilament plastic, 30 denier; and the fiberglass fabric had 23 courses and 14½ wales per inch, and was 446 denier. The six layers of fiberglass fabric together were about 0.20 to 0.25-inch thick, and the double knit-type material was about 0.15-inch thick. Accordingly, the double knit-type material was thinner, stronger and lighter weight than the conventional layered fiberglass casting material.

It is to be understood that the foregoing detailed description and the accompanying drawings relate to preferred embodiments of the invention. Further modifications and variations of the present invention are contemplated, with products similar to double knit material with two surface materials and intermediate spacer filaments or threads being specifically envisioned. Also, instead of stitching, heat bonding, or the use of adhesives may be employed to hold the parts or areas of the supports together. Also, in some cases, the outer channel 42 may be dispensed with, and the straps may be secured to edges of the layered material, or overlapping edges may be provided with VELCRO type material, or eyelets or hooks and laces, to hold the support in place.

With regard to materials which may be used, it is desired that one or both of the outer layers of the double knit-type material be of high strength material, such as fiberglass, kevlar, aramids, or other high strength fibers or materials. The spacer yarns, and one of the two outer layers may be formed of polypropylene, polyester, or nylon. Other materials and yarns may also be used. Concerning the thickness of the double knittype material, it may range from 1/16-inch thickness to ¾-inch thickness, with ⅛-inch to ⅜-inch being preferred. For a finger splint, for example, relatively thin double knit-type material would be used, while for a back brace or support, much thicker material would be employed. It is further noted that the properties of the double knit-type casting material may be changed as desired by (1) altering filament size of the surface yarns or spacer yarns, (2) changing the type of surface knits, (3) changing the density of spacer yarns, (4) interweaving stretchable yarns such as latex to increase strength and recovery, and (5) selectively inlaying high strength fibers such as carbon, kevlar or the like. It is also noted that flat or contoured casting blanks may be knit in a completed form so that the steps of cutting the material and securing against fraying may be avoided. In addition, hardenable material other than water hardenable material may be employed in combination with an appropriate activating agent, with the combination being epoxy or other known two-part polymer hardening systems.

Accordingly, the present invention is not limited to the specific embodiments described hereinabove and shown in the drawings.

What is claimed is:

1. An orthopaedic method comprising the steps of:
   a) preparing an integral double layer fabric having spaced interwoven layers formed of high strength filaments and an open-work matrix of filaments interconnecting said layers, the filaments of said open-work matrix extending back and forth between said two spaced interwoven layers and being interwoven into both of said two spaced interwoven layers, to space said layers apart by a predetermined distance with mostly open space between said two layers except for said spaced filaments said spaced filaments; whereby a water distribution channel is for directing water is located within the double-layered fabric;
   b) said high strength filaments being formed of material selected from the group consisting of fiberglass, kevlar or aramids, with fabrics formed from said materials being subject to fraying at the edges of such fabrics, said edges including arrangements provided for confining and restricting the filaments thereof against fraying;
   c) forming said double layer fabric as a substantially flat blank conforming to the shape of a forearm with a hole to receive the thumb;
   d) impregnating said open-work matrix of filaments with a water-hardenable material under low humidity conditions, while retaining the configuration of said matrix permeable to receive water;
   e) packaging said material in a water vapor impermeable package;
   f) subsequently opening said package;
   g) supplying water to said open-work matrix following opening of said package to rapidly wet said water-hardenable material; and
   h) locating the impregnated double layer material adjacent the injured part of the anatomy so that said material conforms to the configuration of the anatomy;
      whereby the open-work matrix of said double layer fabric facilitates rapid and uniform impregnation by the water-hardenable material, and rapid penetration of the water, and also provides firm support resulting from the hardening of the water-hardenable material in the open-work matrix, and whereby injury from hardened, frayed edges of said high strength filaments is precluded by the edge confining arrangements.

2. An orthopaedic method as defined in claim 1 wherein said method includes the step of providing a shell-shaped member of semi-rigid, flexible material supporting said double layer fabric.

3. An orthopaedic method comprising the steps of:
   a) preparing an integral double layer fabric having spaced interwoven layers formed of high strength filaments and an open-work matrix of filaments interconnecting said layers, the filaments of said open-work matrix extending back and forth between said two spaced interwoven layers and being interwoven into both of said two spaced interwoven layers, to space said layers apart by a predetermined distance with mostly open space between said two layers except for said spaced filaments;
   b) said high strength filaments being formed of material selected from the group consisting of fiberglass, kevlar or aramids, with fabrics formed from said materials being subject to fraying at the edges of such fabrics, said edges including arrangements provided for confining and restricting the filaments thereof against fraying;
   c) forming said double layer fabric as a flat non-rectangular blank having an irregular peripheral shape conforming to a part of the human anatomy requiring support;
   d) impregnating said open-work matrix of filaments with a water-hardenable material under low humidity conditions, while retaining the configuration of said matrix permeable to receive water;
   e) packaging said material in a water vapor impermeable package;
   f) subsequently opening said package;
   g) locating the impregnated double layer material adjacent the injured part of the anatomy so that said material conforms to the configuration of the anatomy; and
   h) supplying water to said open-work matrix following opening of said package to rapidly wet said water-hardenable material;
   whereby the open-work matrix of said double layer fabric facilitates rapid and uniform impregnation by the water-hardenable material, and uniform penetration of the water, and also provides firm support resulting from the hardening of the water-hardenable material in the open-work matrix, and whereby injury from hardened, frayed edges of said high strength filaments is precluded by the edge confining arrangements.

4. An orthopaedic method as defined in claim 3 wherein said method includes the step of providing a shell-shaped member of semi-rigid, flexible material supporting said double layer fabric.

5. An orthopaedic method as defined in claim 3 wherein said method includes forming an assembly including soft goods structure for enclosing said fabric and for holding said assembly onto the portion of the anatomy requiring support.

6. A hardenable soft goods orthopaedic assembly comprising:
   a double layer fabric having spaced interwoven layers and an open-work matrix of fibers interconnecting said layers, the filaments of said open-work matrix extending back and forth between said two spaced interwoven layers and being interwoven into both of said two spaced interwoven layers, to space said layers apart by a predetermined distance with mostly open space between said two layers except for said spaced filaments;
   said double layer fabric being impregnated with water-hardenable material leaving some space within said matrix to receive water;
   a liquid barrier on both sides of said double layer fabric for directing and retaining water applied to said double layer in active contact with said water-hardenable material; and
   said assembly including soft goods structure for enclosing said double layer fabric, and for holding said assembly onto the portion of the anatomy requiring support;
   whereby the open-work matrix of said double layer fabric facilitates rapid and uniform impregnation by the water-hardenable material, and rapid and uniform penetration of the water, and also provides firm support resulting from the hardening of the water-hardenable material in the open-work matrix.

7. An assembly as defined in claim 6 wherein said assembly includes at least one layer of fiberglass material extending along said double layer fabric.

8. An assembly as defined in claim 7 wherein said fiberglass layer forms at least one of the layers of fabric of said double layer fabric.

9. An assembly as defined in claim 7 wherein said layer of fiberglass material is mounted within said assembly adjacent one of said active layers.

10. An assembly as defined in claim 6 further comprising water inlet means for supplying water to substantially all of said water-hardenable material, to conform and set said active layers to the configuration of the portion of the anatomy to be supported.

11. An assembly as defined in claim 6 wherein two layers of said double layer fabric are provided, and a water distribution network is provided between said two layers of double layer fabric.

12. An assembly as defined in claim 6 further comprising water vapor impermeable packaging for enclosing said assembly, for preventing premature activation and hardening of said water-hardenable material during storage prior to intentional activation.

13. A hardenable soft goods orthopaedic assembly comprising:
   an active layer formed of a double layer fabric having spaced interwoven layers and an open-work matrix of fibers interconnecting said layers, the filaments of said open-work matrix extending back and forth between said two spaced interwoven layers and interwoven into both of said two spaced interwoven layers, to space said layers apart by a predetermined distance with mostly open space between said two layers except for said spaced filaments;
   said active layer being impregnated with water-hardenable material;
   said assembly including soft goods structure enclosing said active layer, and holding said assembly onto the portion of the anatomy requiring support; and
   said assembly including an outer flexible covering having mating edges, and straps securely fastened to said covering for holding said edges together;
   whereby the open-work matrix of said active double layer fabric facilitates rapid and uniform impregnation by the water-hardenable material, and uniform penetration of the water, and also provides firm support resulting from the hardening of the water-hardenable material in the open-work matrix.

14. An assembly as defined in claim 13 wherein said assembly includes at least one layer of fiberglass material extending along at least one of said active layers.

15. An assembly as defined in claim 14 wherein said fiberglass layer forms at least one of the layers of fabric of said active layer.

16. An assembly as defined in claim 14 wherein said layer of fiberglass material is mounted within said assembly adjacent said active layer.

17. An assembly as defined in claim 13 further comprising liquid water impermeable layers on both sides of said active layer, to confine the water to be supplied to said water-hardenable material.

18. An assembly as defined in claim 13 further comprising water vapor impermeable packaging for enclosing said assembly, for preventing premature activation and hardening of said water-hardenable material during storage prior to intentional activation.

19. An orthopaedic method comprising the steps of:
   a) forming an integral double layer fabric having spaced interwoven layers formed of high strength filaments and an open-work matrix of filaments interconnecting said layers;
   b) impregnating said openwork matrix of filaments with a hardenable material while retaining the configuration of said matrix permeable to receive an activating agent;
   c) packaging said material in an orthopaedic package;
   d) subsequently opening said package;
   e) supplying an activating agent to said open-work matrix to set said hardenable material; and
   f) locating the impregnated double layer material adjacent the injured part of the anatomy so that said material conforms to the configuration of the anatomy;
      whereby the open-work matrix of said double layer fabric facilitates rapid and uniform impregnation by the hardenable material, and uniform penetration of the activating agent, and also provides firm support resulting from the hardening of the hardenable material in the open-work matrix.

20. A hardenable orthopaedic assembly comprising:
   an active layer formed of a double layer fabric having spaced interwoven layers and an open-work matrix of fibers inter-connecting said layers; said double layer fabric including at least one of (a) said first layer, (b) said second layer, and (c) said matrix, being principally formed of a material selected from the group consisting of (1) fiberglass, (2) kevlar, and (3) aramids, the filaments of said open-work matrix extending back and forth between said two spaced interwoven layers and being interwoven into both of said two spaced interwoven layers, to space said layers apart by a predetermined distance with mostly open space between said two layers except for said spaced filaments;
   said active layer being impregnated with water-hardenable material;
   said spaced layers being independently movable with respect to each other, within the limits of said inter-connecting fibers, for ease in three-dimensional draping around the anatomy;
   soft padding material mounted on one side of said double layer fabric; and
   water vapor impermeable packaging enclosing said impregnated double layer fabric,
   whereby the open-work matrix of said active double layer fabric facilitates rapid and uniform impregnation by the water-hardenable material, and subsequent uniform penetration of water, and also provides firm support resulting from the hardening of the water-hardenable material in the open-work matrix.

21. An orthopaedic method using the assembly as defined in claim 20 and applying it to a patient following opening the packaging and applying water to the assembly.

22. A hardenable orthopaedic assembly comprising:
   an active layer formed of a double layer fabric having spaced interwoven layers and an open-work matrix of fibers inter-connecting said layers; said double layer fabric including at least one of (a) said first layer, (b) said second layer, and (c) said matrix, being principally formed of a material selected from the group consisting of (1) fiberglass, and (2) aramids, the filaments of said open-work matrix extending back and forth between said two spaced interwoven layers and being interwoven into both of said two spaced interwoven layers, to space said layers apart by a predetermined distance with mostly open space between said two layers except for said spaced filaments;
   said active layer being impregnated with water-hardenable material;
   said spaced layers being independently movable with respect to each other, within the limits of said inter-connecting fibers, for ease in three-dimensional draping around the anatomy; and
   water vapor impermeable packaging enclosing said impregnated double layer fabric,
   whereby the open-work matrix of said active double layer fabric facilitates rapid and uniform impregnation by the water-hardenable material, and subsequent uniform penetration of water, and also provides firm support resulting from the hardening of the water-hardenable material in the open-work matrix.

23. A hardenable soft goods orthopaedic assembly comprising:
   a double layer fabric having spaced interwoven layers and an open-work matrix of fibers interconnecting said layers, the filaments of said open-work matrix extending back and forth between said two spaced interwoven layers and being interwoven into both of said two spaced interwoven layers, to space said layers apart by a predetermined distance with mostly open space between said two layers except for said spaced filaments;
   said double layer fabric being impregnated with water-hardenable material leaving some spaced within said matrix to receive water;
   a liquid barrier on both sides of said double layer fabric for directing and retaining water applied to said double layer in active contact with said water-hardenable material; and
   said assembly including soft goods structure having associated straps for at least partially enclosing said double layer fabric, and for holding said assembly onto the portion of the anatomy requiring support;
   said assembly including two layers of said double layer fabric;
   whereby the open-work matrix of said double layer fabric facilitates rapid and uniform impregnation by the water-hardenable material, and rapid and uniform penetration of the water, and also provides firm support resulting from the hardening of the water-hardenable material in the open-work matrix.

24. An orthopaedic method comprising the steps of:
   a) preparing an integral double layer fabric having spaced interwoven layers formed of high strength filaments and an open-work matrix of filaments interconnecting said layers;
   b) forming an assembly including soft goods structure for at least partially enclosing said fabric and for holding said assembly onto the portion of the anatomy requiring support and providing a distribution channel for directing water to said impregnated fabric;
   c) impregnating said open-work matrix of filaments with a water-hardenable material under low humidity conditions, while retaining the configuration of said matrix permeable to receive water;
   d) packaging said material in a water vapor impermeable package;
   e) subsequently opening said package;
   f) supplying water to said open-work matrix following opening of said package to rapidly wet said water-hardenable material; and
   g) locating the impregnated double layer material adjacent the injured part of the anatomy so that said material conforms to the configuration of the anatomy;
      whereby the open-work matrix of said double layer fabric facilitates rapid and uniform impregnation by the water-hardenable material, and uniform penetration of the water, and also provides firm support resulting from the hardening of the water-hardenable material in the open-work matrix.

25. A hardenable soft goods orthopaedic assembly comprising:
   an active layer formed of a double layer fabric having spaced interwoven layers and an open-work matrix of fibers inter-connecting said layers;
   said active layer being impregnated with water-hardenable material;
   said assembly including soft goods structure at least partially enclosing said active layer, and holding said assembly onto the portion of the anatomy requiring support; and
   said assembly further comprising a water distribution structure for supplying water to said active layer;
      whereby the open-work matrix of said active double layer fabric facilitates rapid and uniform impregnation by the water-hardenable material, and uniform penetration of the water, and also provides firm support resulting from the hardening of the water-hardenable material in the open-work matrix.

26. An assembly as defined in claim 25 further comprising water inlet means for supplying water to said distribution network and to substantially all of said water-hardenable material, to conform said active layer to the configuration of the portion of the anatomy to be supported.

27. An orthopaedic method comprising the steps of:
   a) preparing an integral double layer fabric having spaced interwoven layers formed of high strength filaments and an open-work matrix of filaments interconnecting said layers in a single process, the filaments of said open-work matrix extending back and forth between said two spaced interwoven layers and being interwoven into both of said two spaced interwoven layers, to space said layers apart by a predetermined distance with mostly open space between said two layers except for said spaced filaments;
   b) converting said double layer material into a non-rectangular substantially flat blank having an irregular shape to fit a specific portion of the anatomy;
   c) impregnating said open-work matrix of filaments with a water hardenable material under low humidity conditions, while retaining the configuration of said matrix;
   d) packaging said material in a water vapor impermeable package;
   e) subsequently opening said package;
   f) supplying water to said open-work matrix following opening of said package to rapidly wet said water-hardenable material;
      whereby the open-work matrix of said double layer fabric facilitates rapid and uniform impregnation by the water-hardenable material, and rapid dispersement of the water, and also provides firm support resulting from the hardening of the water-hardenable material in the open-work matrix.

28. A hardenable orthopaedic device comprising:
   a) a double layer fabric having spaced apart knit layers formed of high strength filaments and an open-work matrix of filaments interconnecting said layers, the filaments of said open-work matrix extending back and forth between said two spaced interwoven layers and being interwoven into both of said two spaced interwoven layers, to space said layers apart by a predetermined distance with mostly open space between said two layers except for said spaced filaments;
   b) said fabric being created in a single processing step;
   c) said double layer fabric being substantially flat and contoured in a non-rectangular irregular shape to specifically fit at least partially around the portion of the anatomy to be supported;
   d) said double layer fabric being impregnated with water-hardenable material;
      whereby the open-work matrix of said double layer fabric facilitates rapid and uniform impregnation by the water-hardenable material, and rapid penetration of the water, and also provides firm support resulting from the hardening of the water-hardenable material in the open-work matrix.

* * * * *